(12) United States Patent
Takahashi (10) Patent No.: US 9,895,126 B2
(45) Date of Patent: Feb. 20, 2018

(54) SYSTEM AND METHOD FOR QUANTIFICATION OF MUSCLE AND FAT USING ABDOMINAL CT IMAGING

(71) Applicant: MAYO FOUNDATION FOR MEDICAL EDUCATION AND RESEARCH, Rochester, MN (US)

(72) Inventor: Naoki Takahashi, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 15/254,823

(22) Filed: Sep. 1, 2016

(65) Prior Publication Data

US 2017/0055926 A1 Mar. 2, 2017

Related U.S. Application Data

(60) Provisional application No. 62/213,308, filed on Sep. 2, 2015.

(51) Int. Cl.
*G06K 9/00* (2006.01)
*A61B 6/00* (2006.01)
*A61B 6/03* (2006.01)

(52) U.S. Cl.
CPC ............ *A61B 6/5217* (2013.01); *A61B 6/032* (2013.01); *A61B 6/463* (2013.01); *A61B 6/50* (2013.01)

(58) Field of Classification Search
CPC ......... G06T 2207/30004; G06T 7/0012; G06T 2207/10132; G06T 7/11; A61B 6/032
USPC ......... 382/128, 31, 130, 171, 173, 174, 190, 382/199, 203; 600/443; 128/922; 378/4
See application file for complete search history.

(56) References Cited

U.S. PATENT DOCUMENTS

| | | | | |
|---|---|---|---|---|
| 7,545,979 B2 * | 6/2009 | Fidrich | ..................... | G06T 7/12 382/128 |
| 8,270,687 B2 * | 9/2012 | Nakashima | ........... | G06T 7/0012 128/922 |
| 8,483,458 B2 * | 7/2013 | Payne | .................. | A61B 5/4872 128/922 |
| 8,995,739 B2 * | 3/2015 | Xiao | .................... | G06K 9/6267 382/131 |

* cited by examiner

*Primary Examiner* — Charlotte M Baker
(74) *Attorney, Agent, or Firm* — Quarles & Brady LLP (57) ABSTRACT

A system and method for quantifying muscle and fat from abdominal image data. An input is configured to receive the abdominal image data from a CT imaging system. A non-transitive computer-readable storage medium having stored thereon instructions. A processor is configured to receive the abdominal image data and access the storage medium to execute instructions. The executed instructions perform automated segmentation of the abdominal image data into at least one of a subcutaneous fat compartment, a muscle compartment, or a visceral fat compartment. One or more of the compartments are compared to a predetermined threshold to identify corresponding boundaries thereof. An area of one or more of the compartments is calculated based on the corresponding boundaries and predetermined threshold. A display is coupled to the processor and configured to display the at least one subcutaneous fat compartment, muscle compartment, or visceral fat compartment on the abdominal image data.

18 Claims, 7 Drawing Sheets

SYSTEM AND METHOD FOR QUANTIFICATION OF MUSCLE AND FAT USING ABDOMINAL CT IMAGING

CROSS-REFERENCE TO RELATED APPLICATIONS

This application claims priority to U.S. Provisional Patent Application No. 62/213,308, filed Sep. 2, 2015, and entitled "SYSTEM AND METHOD FOR QUANTIFICATION OF MUSCLE AND FAT USING ABDOMINAL CT IMAGING."

STATEMENT REGARDING FEDERALLY SPONSORED RESEARCH

Not applicable.

BACKGROUND OF THE DISCLOSURE

The present disclosure relates to systems and methods for assessing body composition using computed tomography (CT) imaging. More particularly, the disclosure relates to systems and methods for assessing and quantifying abdominal muscle and fat to be used as biomarkers by automatically segmenting a CT scan of the abdomen.

There is a growing interest in the use of body composition (i.e., the amount of muscle and fat) as a biomarker, such as predicting outcome of cancer patients. For example, a wasting syndrome of advanced disease associates with shortened survival. Moreover, certain tissue compartments represent sites for drug distribution and are likely determinants of chemotherapy efficacy and toxicity. CT is considered a gold standard method used to assess body composition because of its high degree of specificity for the separate discrimination of many organs and tissues. However, the use of CT for assessing body composition in non-cancer populations is limited. CT scans of the abdomen are routinely obtained in the staging of cancer patients, and muscle and fat are readily distinguishable from other structures and could be quantified. Although these patients are routinely evaluated by high-resolution diagnostic imaging, the information content of these images is barely exploited, in part owing to lack of deployment of relevant methods and concepts in a cancer care setting.

Conventional manual segmentation of CT images uses defined windows of Hounsfield units (HU, units of radiation attenuation) for each tissue, and is guided by operator knowledge of anatomical structures. Automatic fat segmentation methods have been reported which are relatively straightforward owing to the unique HU ranges of adipose tissues. However, automated quantification of muscle, despite being highly related to human function and disease outcome, is more difficult. This latter task is particularly challenging owing to the large variability in muscle shape and the overlap in HU between muscle on the CT and abdominal organs, such as bowel, kidneys, liver and spleen. While manual segmentation of the muscle area is an option, it is time consuming and not practical for large scale clinical practice or research.

Thus, it would be beneficial to have systems and methods to automatically segment and quantify abdominal muscle and fat from CT images in a time efficient manner.

SUMMARY OF THE DISCLOSURE

The present disclosure overcomes the aforementioned drawbacks by providing systems and methods that allow for semi-automated quantification of abdominal muscle and fat. The systems and methods automatically segment the CT scan of the abdomen into three compartments including an outer-most compartment that contains subcutaneous fat, a middle compartment that contains abdominal wall/paraspinal muscle and spine, and an inner-most compartment that contains visceral fat and internal organs. After segmentation of the three compartments, the amount of muscle can be quantified using, for example, a threshold method as the muscle is the only soft tissue structure in the middle compartment.

In one aspect of the present disclosure, a system for quantifying muscle and fat from abdominal image data is disclosed. The system includes an input configured to receive the abdominal image data from a CT imaging system. The system further includes a non-transitive computer-readable storage medium having stored thereon instructions. A processor is configured to receive the abdominal image data and access the storage medium to execute instructions. The executed instructions perform automated segmentation of the abdominal image data into at least one of a subcutaneous fat compartment, a muscle compartment, or a visceral fat compartment. One or more of the compartments are compared to a predetermined threshold to identify corresponding boundaries thereof. An area of one or more of the compartments is calculated based on the corresponding boundaries and predetermined threshold. A display is coupled to the processor and configured to display the at least one subcutaneous fat compartment, muscle compartment, or visceral fat compartment on the abdominal image data.

In another aspect of the present disclosure a method for quantifying muscle and fat from abdominal image data is disclosed. The method includes acquiring abdominal image data from a CT imaging system. The method further includes performing, using a processor coupled to the CT imaging system, automated segmentation of the abdominal image data into at least one of a subcutaneous fat compartment, a muscle compartment, or a visceral fat compartment. The at least one subcutaneous fat compartment, muscle compartment, or visceral fat compartment is compared to a predetermined threshold to identify corresponding boundaries thereof. An area of the at least one subcutaneous fat compartment, muscle compartment, or visceral fat compartment is calculated based on the corresponding boundaries and predetermined threshold. The at least one subcutaneous fat compartment, muscle compartment, or visceral fat compartment is displayed on the abdominal image data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE DISCLOSURE

Figure 1A:
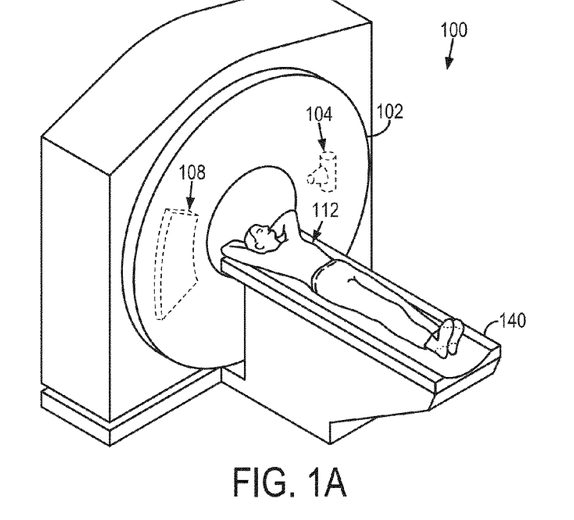
FIGS. 1A and 1B illustrate an example CT system that can be configured to implement the present disclosure.
Figure 1B:
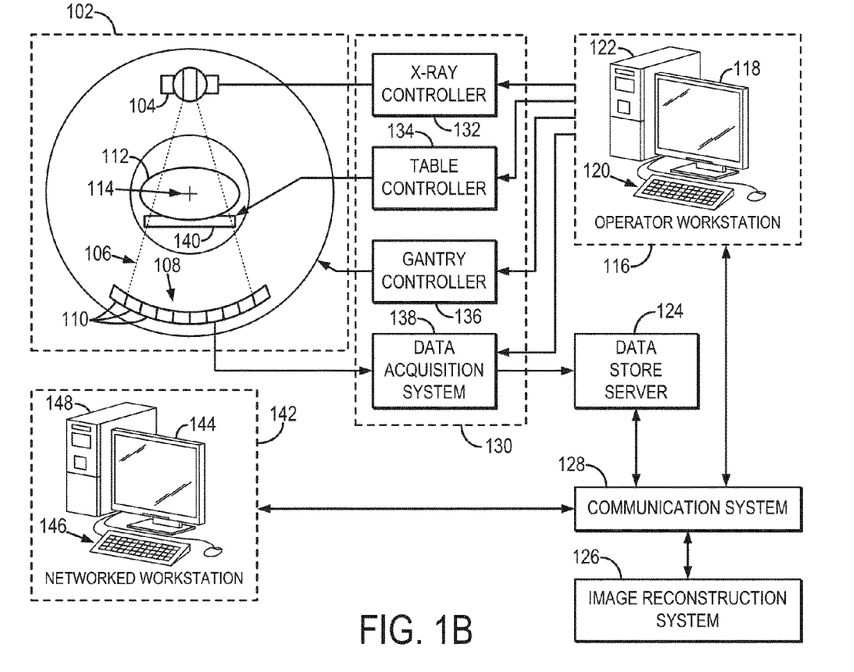

Referring particularly now to FIGS. 1A and 1B, an example of an x-ray computed tomography ("CT") imaging system 100 that may be used to implement the present disclosure is illustrated. The CT imaging system 100 includes a gantry 102, to which at least one x-ray source 104 is coupled. The x-ray source 104 projects an x-ray beam 106, which may be a fan-beam or cone-beam of x-rays, towards a detector array 108 on the opposite side of the gantry 102. The detector array 108 includes a number of x-ray detector elements 110. Together, the x-ray detector elements 110 sense the projected x-rays 106 that pass through a subject 112, such as a medical patient or an object undergoing examination, that is positioned in the CT system 100. Each x-ray detector element 110 produces an electrical signal that may represent the intensity of an impinging x-ray beam and, hence, the attenuation of the beam as it passes through the subject 112. In some configurations, each x-ray detector 110 is capable of counting the number of x-ray photons that impinge upon the detector 110. During a scan to acquire x-ray projection data, the gantry 102 and the components mounted thereon rotate about a center of rotation 114 located within the CT system 100.

The CT system 100 also includes an operator workstation 116, which typically includes a display 118; one or more input devices 120, such as a keyboard and mouse; and a computer processor 122. The computer processor 122 may include a commercially available programmable machine running a commercially available operating system. The operator workstation 116 provides the operator interface that enables scanning control parameters to be entered into the CT system 100. In general, the operator workstation 116 is in communication with a data store server 124 and an image reconstruction system 126. By way of example, the operator workstation 116, data store server 124, and image reconstruction system 126 may be connected via a communication system 128, which may include any suitable network connection, whether wired, wireless, or a combination of both. As an example, the communication system 128 may include both proprietary or dedicated networks, as well as open networks, such as the internet.

The operator workstation 116 is also in communication with a control system 130 that controls operation of the CT system 100. The control system 130 generally includes an x-ray controller 132, a table controller 134, a gantry controller 136, and a data acquisition system ("DAS") 138. The x-ray controller 132 provides power and timing signals to the x-ray source 104 and the gantry controller 136 controls the rotational speed and position of the gantry 102. The table controller 134 controls a table 140 to position the subject 112 in the gantry 102 of the CT system 100.

The DAS 138 samples data from the detector elements 110 and converts the data to digital signals for subsequent processing. For instance, digitized x-ray data is communicated from the DAS 138 to the data store server 124. The image reconstruction system 126 then retrieves the x-ray data from the data store server 124 and reconstructs an image therefrom. The image reconstruction system 126 may include a commercially available computer processor, or may be a highly parallel computer architecture, such as a system that includes multiple-core processors and massively parallel, high-density computing devices. Optionally, image reconstruction can also be performed on the processor 122 in the operator workstation 116. Reconstructed images can then be communicated back to the data store server 124 for storage or to the operator workstation 116 to be displayed to the operator or clinician.

The CT system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 116, or in a different facility, such as a different healthcare institution or clinic.

The networked workstation 142, whether within the same facility or in a different facility as the operator workstation 116, may gain remote access to the data store server 124 and/or the image reconstruction system 126 via the communication system 128. Accordingly, multiple networked workstations 142 may have access to the data store server 124 and/or image reconstruction system 126. In this manner, x-ray data, reconstructed images, or other data may be exchanged between the data store server 124, the image reconstruction system 126, and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Figure 2:
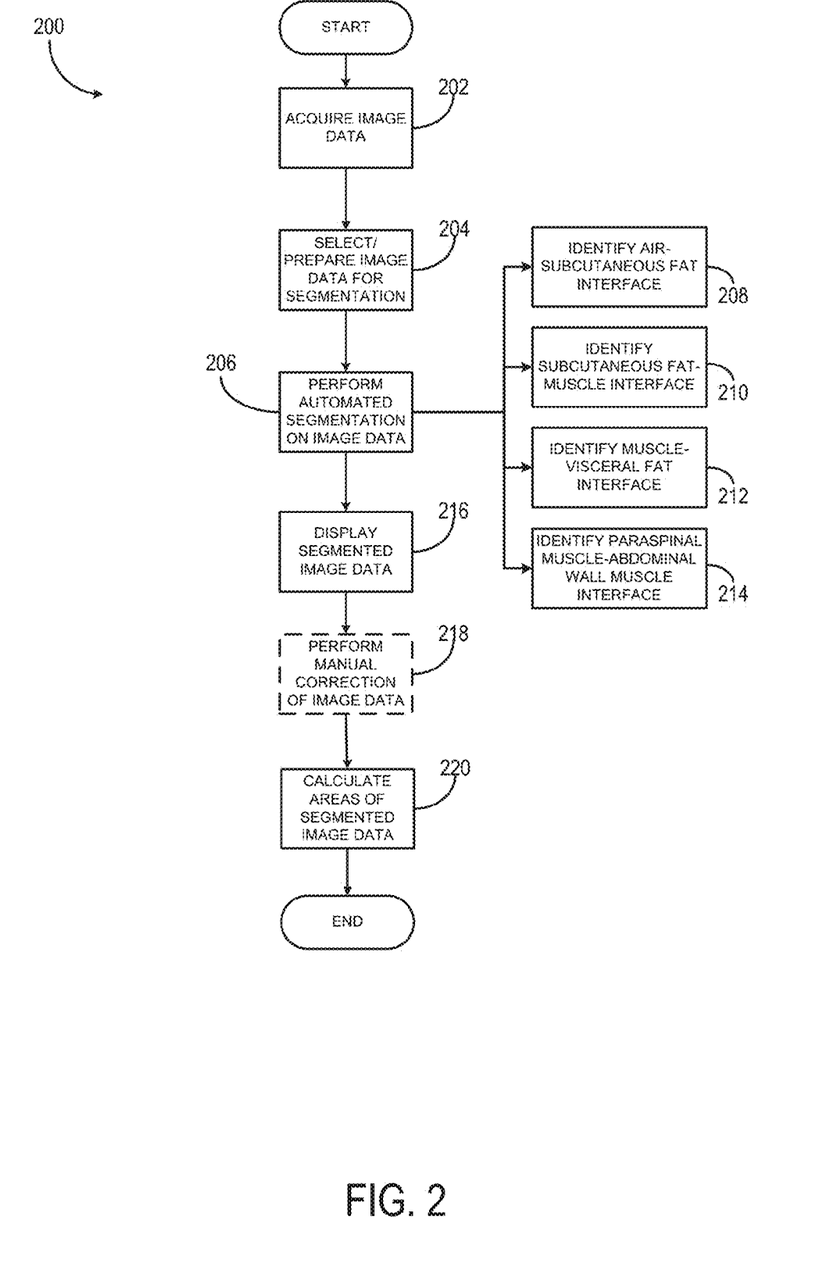
FIG. 2 is a flow chart setting forth the steps of processes for automating segmentation and quantification of abdominal muscle and fat.

Referring now to FIG. 2, a flow chart setting for exemplary steps 200 for automating segmentation and quantification of abdominal muscle and fat is provided. To start the process, image data, such at abdominal CT image data, may be acquired at process block 202. The image data may be collected from the CT imaging system 100 shown in FIGS. 1A and 1B, for example. Once the image data is acquired, a user may select and prepare the desired image data for segmentation at process block 204. In one non-limiting example, the user may select the desired image data from a user interface, such as a graphical user interface (GUI), provided by the operator workstation 116 shown in FIG. 1B. The image data may be selected from a folder provided on the user interface containing multiple CT images of a patient. For example, the user may select an appropriate CT series that contains multiple CT dicom images displayed in the axial and sagittal plane. The user may then scroll through the CT images to select an appropriate CT image at a desired level (e.g., third lumbar spine level (L3)).

Figure 3:
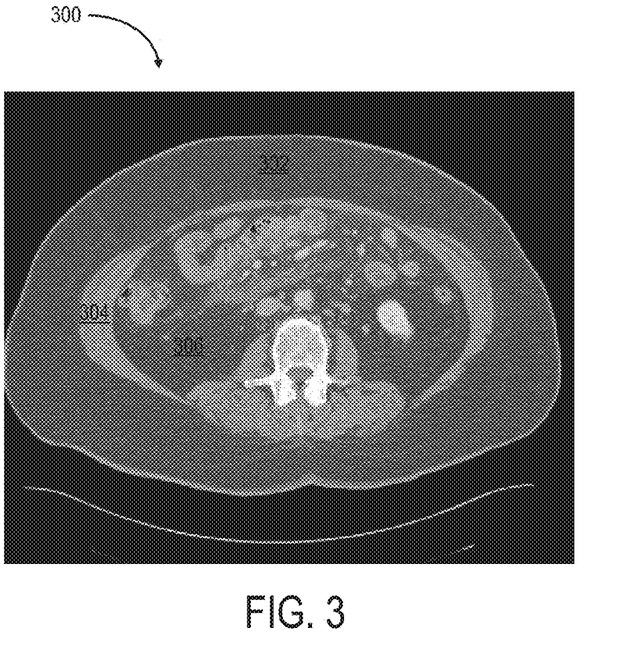
FIG. 3 is an exemplary abdominal CT image that includes a subcutaneous fat compartment, a muscle compartment, and a visceral fat compartment.

An exemplary abdominal CT image 300 is shown in FIG. 3 and includes a subcutaneous fat compartment 302, a muscle compartment 304 including the paraspinal muscle and spine, and a visceral fat compartment 306. Once the image data is selected, a smoothing filter may be applied to the selected image, such as image 300, to reduce noise for image preparation at process block 204. Additionally, the total area of fat may be calculated from the image 300 in order to prepare the image at process block 204. The total area of fat may be used later in the process to determine thresholds, as will be described in further detail below.

Figure 4:
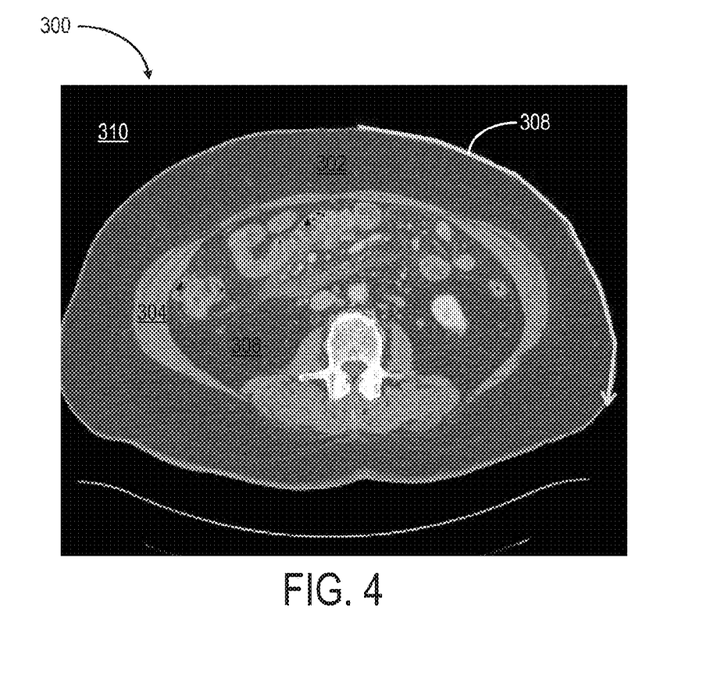
FIG. 4 is the exemplary abdominal CT image of FIG. 3 showing an air-subcutaneous fat interface between a compartment of air and the subcutaneous fat compartment of the image.

Next, at process block 206, automated image segmentation may be performed on the image data. For example, image segmentation may be performed on the image 300 shown in FIG. 3 to automatically identify the various compartments 302, 304, 306 of the abdomen. The automated image segmentation process may begin by first identifying an air-subcutaneous fat interface at process block 208. An exemplary air-subcutaneous fat interface 308 is shown in FIG. 4 between a compartment of air 310 and the subcutaneous fat compartment 302 of the image 300. In order to identify the air-subcutaneous fat interface 308 at process block 208, air density may be replaced with 0, and non-air density/tissue may be replaced with 1 using, for example, CT attenuation values from −200 to −30 HU for fat. For example, −200 HU may be used as a threshold to differentiate air and non-air compartments. Holes within body (non-air tissue) may be filled, and small objects and any structure outside the body may be removed from the image 300. The air-subcutaneous fat interface 308 may then be saved on the data store server 124 of FIG. 1B, for example, as a perimeter having a boundary between 0 and 1.

Figure 5:
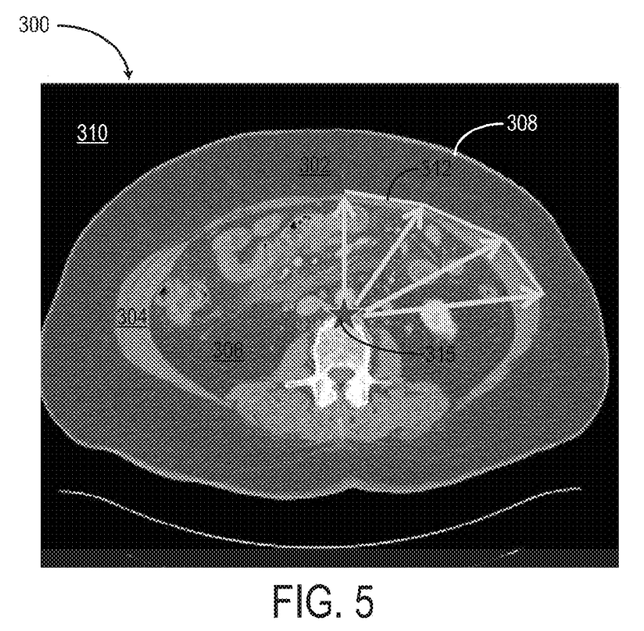
FIG. 5 is the exemplary abdominal CT image of FIG. 3 showing a subcutaneous fat-muscle interface between the subcutaneous fat compartment and the muscle compartment of the image obtained from radial scanning from a centroid of the image 300.

Next, at process block 210, a subcutaneous fat-muscle interface may be identified. An exemplary subcutaneous fat-muscle interface 312 is shown in FIG. 5 between the subcutaneous fat compartment 302 and the muscle compartment 304 of the image 300. In order to identify the subcutaneous fat-muscle interface 312 at optional process block 210, air density and fat density may be replaced with 0, and soft tissue may be replaced with 1 using, for example, CT attenuation values from −200 to −30 HU for fat and −30 to 200 HU for muscle. However, process block 210 is optional and does not need to be performed. In one non-limiting example, a mask may be created using the previously generated air-subcutaneous fat interface 308 and any structure outside the air-subcutaneous fat interface 308 may be replaced with air. Radial scanning may be performed from 0 to 360 degrees from a centroid 315 of the subcutaneous fat-air interface perimeter, and soft tissue pixels that are farthest away from the centroid 315 may be identified. In one example, the outer most pixels above a threshold may be detected in order to identify the subcutaneous fat-muscle interface 312, where a threshold of −80 Hounsfield units (HU) is used for the anterior abdominal wall and a threshold of −30 HU is used for posterior abdominal wall. Different threshold values may be used for the anterior and posterior abdominal wall because the anterior muscle is often thinner and more difficult to detect compared to posterior muscle. Next, Fourier fitting may be used to generate the subcutaneous fat-muscle interface 312 along the detected pixels in order to eliminate noise and outliers. The previously generated radial image may then be converted into a Cartesian coordinate image, for example, and the detected pixels may be connected to form a circular line representative of the subcutaneous fat-muscle interface 312.

In some embodiments, the lumbar level of the image 300 may also be determined at process block 210, which may be used later to quantify the abdominal muscle and fat. To determine the lumbar level, the previously described radial scanned image may be used to select the paraspinal area near the subcutaneous fat-muscle interface 312. Next, high density structures (i.e., bone) of different sizes (e.g., iliac bone vs. ribs) may be quantified, and based on this data, the level of slice (i.e., Lumbar 1, 3, or 5) may be determined.

Returning to FIG. 2, once the subcutaneous fat-muscle interface 312 is identified at process block 210, a muscle-visceral fat interface may be identified at process block 212. An exemplary muscle-visceral fat interface 314 is shown in FIG. 8 between the muscle compartment 304 and the visceral fat compartment 306 of the image 300. In order to identify the muscle-visceral fat interface 314 at process block 212, an analysis may be performed on an anterior half and posterior half in separate process; however, they the process need not be separated. If separate anterior and posterior processes are performed, identification of anterior edge of spine is performed as part of identifying the posterior half of the interface.

More specifically, to identify the anterior part of muscle-visceral fat interface 314 of the abdominal image 300, a mask may be created using the subcutaneous fat-muscle interface 312. The mask may be created using a thresholds of, as a non-limiting example, −70 HU. That is, compartments outside subcutaneous fat-muscle interface 312 is replaced with values of, as a non-limiting example 500 HU (and, an as-will-be-described spine mask, as 0 HU). Then, the −70 HU threshold is to identify fat. In some situations, 100 to 400 HU may also considered as fat, in order to help identify internal organs such as bowel and liver.

Figure 7:
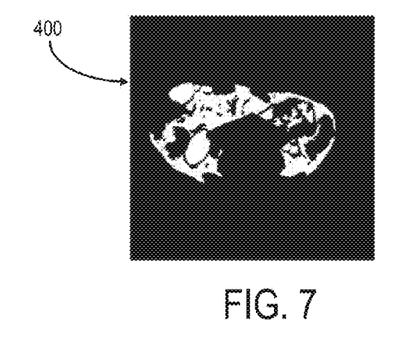
FIG. 7 is an exemplary image of a mask showing removal of small size fat that may be considered part of visceral fat.

That is, a spine mask may be created to mask the fat around the spine, and may be about 112 pixels wide at a midline and about 100 pixels tall from the posterior edge of the subcutaneous fat-muscle interface 312. Next, a fat only image may be created using, for example, a threshold of less than −70 HU in order to help identify high density internal organs, such as bowel and liver. An exemplary fat only image 400 is shown in FIG. 7. For lumbar level 3, any high density structure (e.g., kidney, liver, small bowel, etc.) may be replaced as fat, and for lumbar level 1 and 5, any high density structures may be replaced as soft tissue. This may help identify high density internal organs, such as bowel and the liver.

Alternatively, if the optional process described above with respect to process block 210 is performed and there is a replacement of 1's and 0's, any structure outside the subcutaneous fat-muscle interface 312 may be replaced with soft tissue. In other words, anything outside the subcutaneous fat-muscle interface 312 may be replaced with 1, soft tissue density may be replaced with 1, and fat may be replaced with 0.

Figure 6:
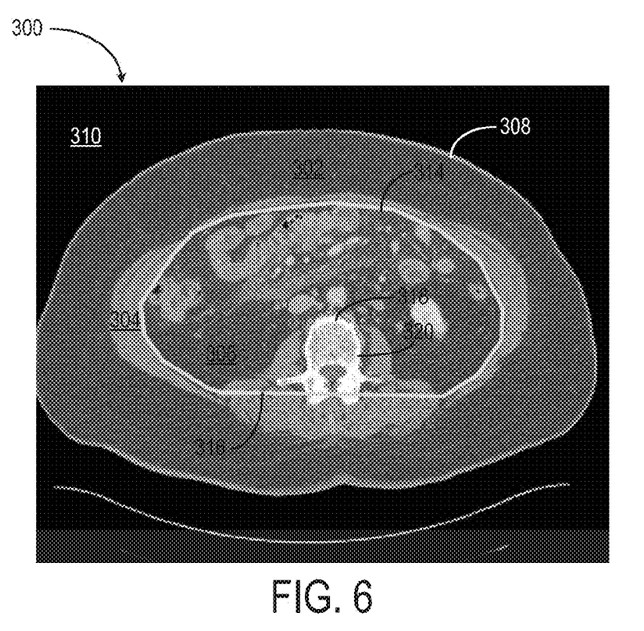
FIG. 6 is the exemplary abdominal CT image of FIG. 3 showing a muscle-visceral fat interface between the muscle compartment and the visceral fat compartment of the image.

Next, a mask that is about half the size of the subcutaneous fat-muscle interface 312 may be created. The area of the mask 400 may be replaced with 1 (i.e., fat) to ensure connection of most intra-abdominal fat. Small size fat in the muscle compartment 304, for example, may be removed from the mask 400 by utilizing a size threshold (i.e., the total area of fat the image 300 previously calculated at process block 204) in order to eliminate fat in the abdominal wall that could be considered as part of visceral fat. Next, the peripheral most points/pixels of fat may be connected to each other using an alpha-shape function for fat pixels without allowing concavity. This allows exclusion of internal organs, as well as exclusion of the paraspinal area by identifying a gap, shown as the longest line 316 (see FIG. 6) in the posterior half of the image 300 and that crosses midline. This allows delineation of anterior part of muscle-visceral fat interface. As noted in FIG. 6, the delineation of muscle-visceral fat interface is inaccurate at this step. Therefore, the longest straight line 316 (see FIG. 6) in the posterior half of the image 300 and that crosses midline may be removed from this boundary.

Figure 8A:
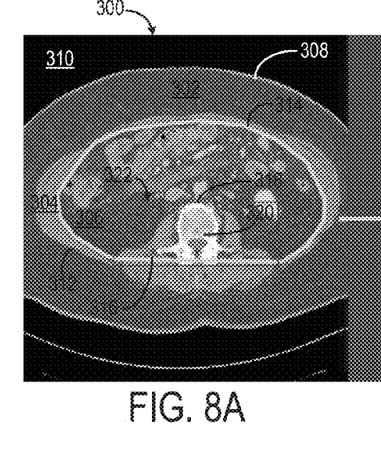
FIGS. 8A-8C show the exemplary abdominal CT image of FIG. 3 including a posterior half of the muscle-visceral fat interface within a paraspinal area.

Next, the posterior half of the muscle-visceral fat interface 314 may be identified to complete the entire muscle-visceral fat interface 314. As shown in FIG. 8A, a paraspinal area 322, as indicated by the rectangular box, may be identified. The paraspinal area 322 may be defined by the longest line 316 in the posterior half of the image 300 and that crosses the midline from the anterior half of the muscle-visceral fat interface 314 for lumbar level 1 and 3 or the iliac crests for lumbar level 5. The anterior edge of the paraspinal area 322 may be defined by the anterior edge 318 of the spine 320 or iliac crest for lumbar level 5. This is done by using a threshold of about 70 HU for lumbar level 5 and a threshold of about 150 HU for lumbar levels 1 and 3. The anterior most pixels may be identified and dilated for connection, and small objects may be removed from the image 300 to reduce noise.

The posterior edge of the paraspinal area 322 may be defined by the posterior edge of the subcutaneous fat-muscle interface 312.

Figure 8B:
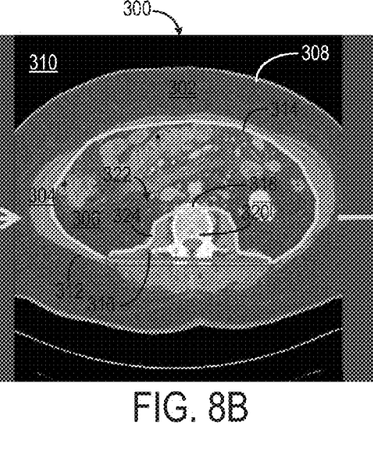
Figure 9:
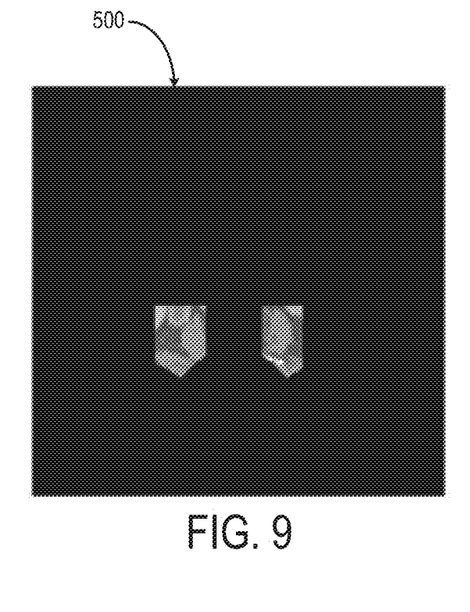
FIG. 9 is an exemplary cropped CT image including a portion of the paraspinal area with modified pixel values.
Figure 10:
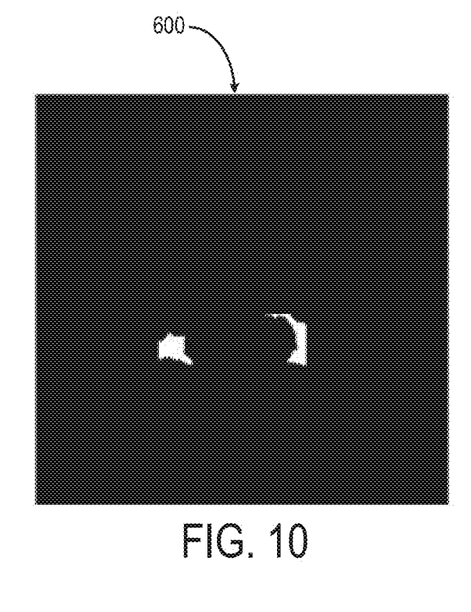
FIG. 10 is an exemplary fat only CT image created using a threshold value to identify the fat and soft tissue interface in the paraspinal area.

Once the paraspinal area 322 is identified, the image 300 may be cropped to the paraspinal area and the pixel values may be modified. For example, the area excluded from the paraspinal area 322 may be replaced by 1,000 HU and high density structures (i.e., greater than 80 HU) may be replaced by fat. An exemplary cropped image 500 including the paraspinal area with modified pixel values is shown in FIG. 9. Next, as shown in FIG. 10, a fat only image 600 may be created using a threshold of about −50 to about −300 HU in order to identify the fat and soft tissue interface in the paraspinal area. Small fat (i.e., fat having a size threshold less than half of the total area of fat) may then be removed from the image 600. The image 600 may then be divided into two portions (i.e., a right and left portion). Each portion of the image may then be scanned from medline to outwardto identify a first fat pixel containing fat and then scanned from posterior to anterior to identify the first pixel containing fat. The pixels are then combined to form a posterior half 324 of the muscle-visceral fat interface 314, as best shown in FIG. 8B.

Figure 8C:
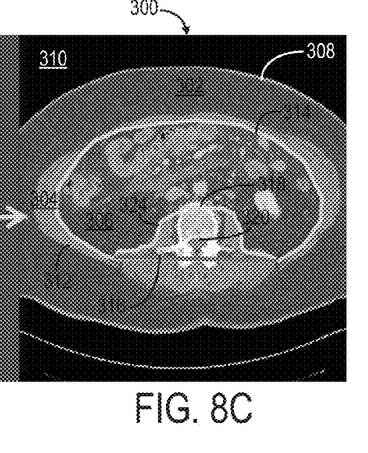

Next, the anterior half of the abdominal image 300, the anterior edge 318 of the spine 320, and the posterior half 324 of the abdominal image 300 may be combined, as shown in FIG. 8C, to form the boundaries of the muscle-visceral fat interface 314. In some embodiments, the processor 122 of FIG. 1, for example, may be configured to determine whether the boundaries of the muscle-visceral fat interface 314 are closed. If the boundaries of the muscle-visceral fat interface 314 are not closed, the processor 122 of FIG. 1 may be configured to identify the endpoints of the open boundary and quantify the number of separate line segments. In one non-limiting example, the two endpoints with the shortest line may be connected. If the number of separate line segments is reduced, the connected line may be retained. This process may be repeated until the boundaries of the muscle-visceral fat interface 314 are closed.

Returning to FIG. 2, if the boundaries of the muscle-visceral fat interface 314 are closed, a paraspinal muscle-abdominal wall muscle interface may then be identified at process block 214. Similar to identifying the muscle-visceral fat interface 314 at process block 242, identifying the paraspinal muscle-abdominal wall muscle interface may include identifying a paraspinal muscle area 326, as indicated by the rectangular box, in FIG. 11. The paraspinal muscle area 326 may be defined by the longest line 316 in the posterior half of the image 300 and that crosses the midline from the anterior half of the muscle-visceral fat interface 314 for lumbar level 1 and 3 or the iliac crests for lumbar level 5. The anterior edge of the paraspinal muscle area 326 may be defined by the anterior edge 318 of the spine 320 or iliac crest for lumbar level 5 with some cushion. The posterior edge of the paraspinal muscle area 326 may be defined by the posterior edge of the subcutaneous fat-muscle interface 312 with some cushion.

Figure 12A:
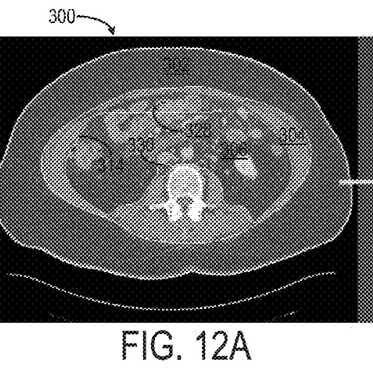
FIGS. 12A-12C are the exemplary CT image of FIG. 3 indicating possible manual adjustment of the muscle-visceral fat interface at an anterior location and a posterior location on the image.

Once the paraspinal muscle-abdominal wall muscle interface is identified at process block 214, the segmented image data may be displayed over the image 300 at process block 216. The image 300 is shown in FIG. 12A including exemplary segments (i.e., air-subcutaneous fat interface 308, subcutaneous fat-muscle interface 312, muscle-visceral fat interface 314, and muscle-abdominal wall muscle interface 326) displayed over the image 300. The segmented image may be displayed to a user on the display 118 of the operator workstation 116 of FIG. 1, for example.

Figure 12B:
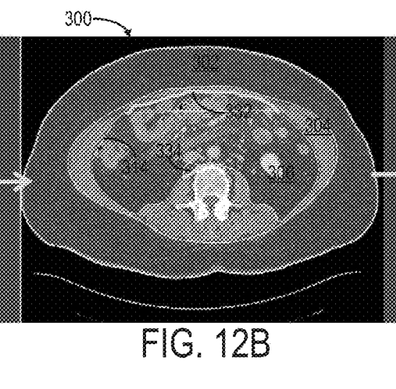
Figure 12C:
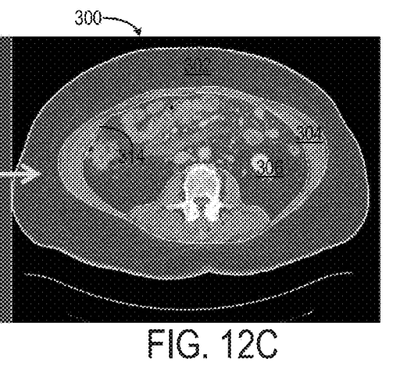

At optional process block 218, the system may prompt the user to perform manual correction of the image data. If the user believes manual correction is necessary, any of the boundaries (i.e., air-subcutaneous fat interface 308, subcutaneous fat-muscle interface 312, muscle-visceral fat interface 314, and muscle-abdominal wall muscle interface 326) may be corrected and updated using the GUI on the operator workstation 116. In one non-limiting example, as shown in FIGS. 12A, 12B and 12C, a user may manually adjust the muscle-visceral fat interface 314 at an anterior location 328 and a posterior location 330 on the image 300 to a new anterior location 332 and posterior location 334.

Figure 11:
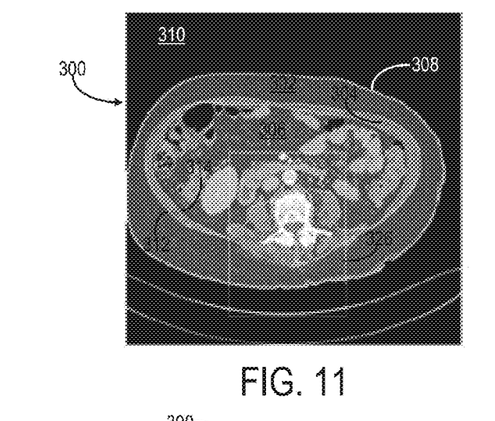
FIG. 11 is another exemplary abdominal CT image showing a paraspinal muscle-abdominal wall muscle interface having a paraspinal muscle area.

Returning to FIG. 2, once manual correction of the image data is performed at optional process block 218, the processor 122 may be configured to calculate areas of the segmented image data at process block 220. In one non-limiting example, four areas may be calculated. As shown in FIG. 11, a first area may be defined by the subcutaneous fat compartment 302 positioned between the air-subcutaneous fat interface 308 and the subcutaneous fat-muscle interface 312. A second area may be defined by the visceral fat compartment 306 within the muscle-visceral fat interface 314. A third area may be defined by the muscle compartment 304 positioned between the subcutaneous fat-muscle interface 312 and the muscle-visceral fat interface 314. And a fourth area may be defined by the paraspinal muscle compartment 326 positioned between the paraspinal muscle compartment boundary and the subcutaneous fat-muscle interface 312 and the muscle-visceral fat interface 314.

In order to calculate areas of the segmented image, masks may be created for each of the four areas. For the first, subcutaneous fat compartment 302 area, a mask may be created for the area between the air-subcutaneous fat interface 308 and the subcutaneous fat-muscle interface 312 and the area from an out of bound extension (e.g., if the body extends outside the scan range). For example, if the air-subcutaneous fat interface 308 extends to the edge of the image 300, pixel locations at the edge of the image 300 and inside the edge of the image 300 may be identified and the area out of bound may be calculated. For the second, visceral fat compartment 306, a mask may be created for and applied to the area within the muscle-visceral fat interface 314. This mask may be, for example, a colonic mask that utilizes the image 300 to identify low density objects (e.g., air −200 HU) and replace the air with, for example, −3000 HU to reduce fat attenuation due to partial volume from air within the bowel.

For the third, muscle compartment 304 area, a mask may be created for and applied to the area between the subcutaneous fat-muscle interface 312 and the muscle-visceral fat interface 314. This mask may be, for example, a spine and bone mask that utilizes the image 300 to identify high density objects (e.g., about 80 HU) and remove small objects (i.e., less thank about 100 pixels). To reduce soft tissue density within the bone and enclosed spinal canal, holes of the identified objects may be filled in. Lastly, the number of pixels within the HU thresholds (e.g., −190 to −30 HU for fat and −30 to 140 HU for muscle) in each of the four compartments 302, 304, 306, 326 may be quantified to determine the area of muscle and fat.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for quantifying muscle and fat from abdominal image data, the system comprising:
an input configured to receive the abdominal image data from a CT imaging system;
a non-transitive computer-readable storage medium having stored thereon instructions;
a processor configured to receive the abdominal image data and access the non-transitive computer-readable storage medium to execute instructions to carry out the steps of:
perform automated segmentation of the abdominal image data into at least one of a subcutaneous fat compartment, a muscle compartment, or a visceral fat compartment;
compare the at least one subcutaneous fat compartment, muscle compartment, or visceral fat compartment to a predetermined threshold to identify corresponding boundaries thereof;
calculate an area of the at least one subcutaneous fat compartment, muscle compartment, or visceral fat compartment based on the corresponding boundaries and predetermined threshold; and
a display coupled to the processor and configured to display the at least one subcutaneous fat compartment, muscle compartment, or visceral fat compartment on the abdominal image data.

2. The system as recited in claim 1 wherein the corresponding boundaries are identified using at least one of CT attenuation thresholding, Fourier fitting, or an alpha-shape function.

3. The system as recited in claim 1 wherein the predetermined threshold for muscle is between about −30 and about 200 Hounsfield units and the predetermined threshold for fat is between about −200 and about −30 Hounsfield units.

4. The system as recited in claim 1 wherein the corresponding boundaries include at least one of an air-subcutaneous fat interface, a subcutaneous fat-muscle interface, muscle-visceral fat interface, or muscle-abdominal wall muscle interface.

5. The system as recited in claim 4 wherein the subcutaneous fat-muscle interface is identified using a radial scanned image created from a centroid thereof.

6. The system as recited in claim 4 wherein the muscle-visceral fat interface includes an anterior portion, a posterior portion, and an anterior edge of a spine, the anterior portion created using an alpha-shape function to identify and connect peripheral most points of the corresponding boundary.

7. The system as recited in claim 6 wherein the posterior portion of the muscle-visceral fat interface is created by identifying a paraspinal area defined by an anterior edge of the spine, a posterior edge of the subcutaneous fat-muscle interface, and a line extending across the anterior portion of the muscle-visceral fat interface.

8. The system as recited in claim 1 wherein the processor is further configured to create at least one mask for the at least one subcutaneous fat compartment, muscle compartment, or visceral fat compartment to calculate the area, the at least one mask including at least one of a colonic mask or a spine and bone mask.

9. The system as recited in claim 1 further comprising a manual correction tool on the display for manually correcting the corresponding boundaries.

10. A method for quantifying muscle and fat from abdominal image data, the method comprising the steps of:
acquiring abdominal image data from a CT imaging system;
performing, using a processor coupled to the CT imaging system, automated segmentation of the abdominal image data into at least one of a subcutaneous fat compartment, a muscle compartment, or a visceral fat compartment;
comparing the at least one subcutaneous fat compartment, muscle compartment, or visceral fat compartment to a predetermined threshold to identify corresponding boundaries thereof;
calculating an area of the at least one subcutaneous fat compartment, muscle compartment, or visceral fat compartment based on the corresponding boundaries and predetermined threshold; and
displaying the at least one subcutaneous fat compartment, muscle compartment, or visceral fat compartment on the abdominal image data.

11. The method as recited in claim 10 wherein the corresponding boundaries are identified using at least one of CT attenuation thresholding, Fourier fitting, or an alpha-shape function.

12. The method as recited in claim 10 wherein the predetermined threshold for muscle is between about −30 and about 200 Hounsfield units and the predetermined threshold for fat is between about −200 and about −30 Hounsfield units.

13. The method as recited in claim 10 wherein the corresponding boundaries include at least one of an air-subcutaneous fat interface, a subcutaneous fat-muscle interface, muscle-visceral fat interface, or muscle-abdominal wall muscle interface.

14. The method as recited in claim 13 wherein the subcutaneous fat-muscle interface is identified using a radial scanned image created from a centroid thereof.

15. The method as recited in claim 13 wherein the muscle-visceral fat interface includes an anterior portion, a posterior portion, and an anterior edge of a spine, the anterior portion created using an alpha-shape function to identify and connect peripheral most points of the corresponding boundary.

16. The method as recited in claim 15 wherein the posterior portion of the muscle-visceral fat interface is created by identifying a paraspinal area defined by an anterior edge of the spine, a posterior edge of the subcutaneous fat-muscle interface, and a line extending across the anterior portion of the muscle-visceral fat interface.

17. The method as recited in claim 10 further including creating at least one mask for the at least one subcutaneous fat compartment, muscle compartment, or visceral fat compartment to calculate the area, the at least one mask including at least one of a colonic mask or a spine and bone mask.

18. The method as recited in claim 10 further including correcting the corresponding boundaries using a manual correction tool.

* * * * *